United States Patent
Fitzgerald et al.

(10) Patent No.: US 6,498,010 B1
(45) Date of Patent: Dec. 24, 2002

(54) METHOD FOR MAKING A DEVICE FOR THE SIMULTANEOUS DETECTION OF MULTIPLE ANALYTES

(75) Inventors: Stephen Peter Fitzgerald, Co. Antrim (GB); John Victor Lamont, Co. Antrim (GB); Robert Ivan McConnell, Co. Antrim (GB); El Ouard Benchikh, Co. Antrim (GB)

(73) Assignee: Randox Laboratories, LTD, Antrim (GB)

( * ) Notice: Subject to any disclaimer, the term of this patent is extended or adjusted under 35 U.S.C. 154(b) by 0 days.

(21) Appl. No.: 09/413,799

(22) Filed: Oct. 7, 1999

Related U.S. Application Data

(62) Division of application No. 09/061,171, filed on Apr. 16, 1998.

(30) Foreign Application Priority Data

Apr. 16, 1998 (EP) .............................................. 97302707

(51) Int. Cl.[7] .............................................. G01N 33/53
(52) U.S. Cl. ........................... 435/6; 436/514; 436/518; 436/524; 436/535; 436/173; 436/172; 436/169; 435/4; 435/7.1; 422/50; 427/261; 427/287; 427/387; 427/407.2
(58) Field of Search ................................ 436/173, 172, 436/169, 518, 524–535; 435/4, 7.1; 422/50; 427/261, 287, 387, 407.2

(56) References Cited

U.S. PATENT DOCUMENTS

| | | | |
|---|---|---|---|
| 4,829,010 A | | 5/1989 | Chang |
| 5,077,210 A | | 12/1991 | Eigler et al. |
| 5,432,099 A | * | 7/1995 | Ekins ..................... 436/518 |
| 5,624,711 A | * | 4/1997 | Sundberg et al. ......... 427/261 |

FOREIGN PATENT DOCUMENTS

| | | | | |
|---|---|---|---|---|
| EP | 127438 | * | 5/1984 | .......... G01N/33/54 |
| EP | A-127 438 | | 12/1984 | |
| EP | A-768 530 | | 4/1997 | |
| FR | A-2-693 740 | | 1/1994 | |
| GB | 2 099 578 A | | 12/1982 | |
| WO | WO 84/0315 | | 8/1984 | |
| WO | WO 90/0156 | | 2/1990 | |
| WO | WO 94/03807 | | 2/1994 | |
| WO | WO 94/23298 | | 10/1994 | |
| WO | WO 94/27137 | | 11/1994 | |
| WO | WO 94/27719 | * | 12/1994 | ............ B01J/19/00 |
| WO | WO 95/16204 | * | 6/1995 | .......... G01N/33/543 |

OTHER PUBLICATIONS

Parsons et al., "Multianalyte Assay System Developed for Drugs of Abuse," Clinical Chemistry 39(9): 1899–1903 (1993).

Buechler et al., "Simultaneous Detection of Seven Drugs of Abuse by the Triage Panel for Drugs of Abuse," Clinical Chemistry 38(9): 1678–1684 (1992).

Hook et al., Silanization of Radio Frequency Glow Discharge Modified Expanded Poly(Tetrafluoroethylene) Using (Aminopropyl)triethoxysilane, Langmuir, vol. 7, No. 1 (1991).

* cited by examiner

*Primary Examiner*—Bao-Thuy L. Nguyen
(74) *Attorney, Agent, or Firm*—Oliff & Berridge, PLC

(57) ABSTRACT

A solid state device for performing multi-analyte assays, comprises a substrate and a multiplicity of discrete reaction sites each bearing a ligand covalently bonded to the substrate, wherein the surface of the substrate between the reaction sites is inert with respect to analyte. Such a device may be obtained by a process of activating the surface of the substrate, and applying an array of ligands on to discrete areas on the surface.

20 Claims, 10 Drawing Sheets

Fig.1.
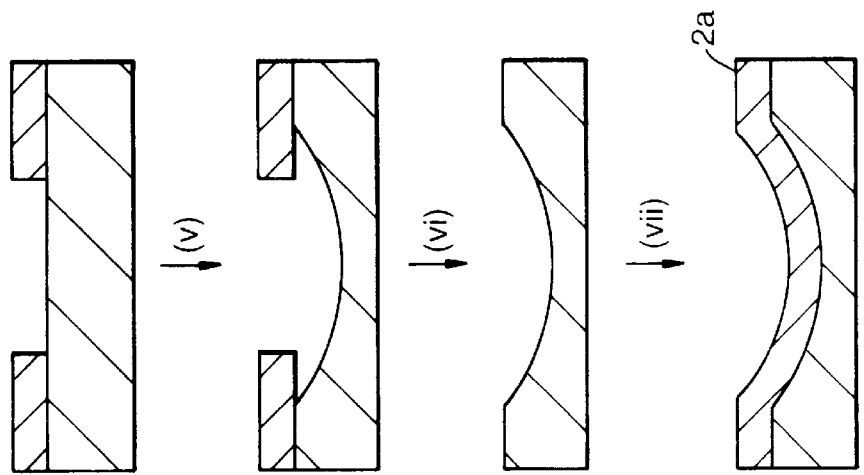
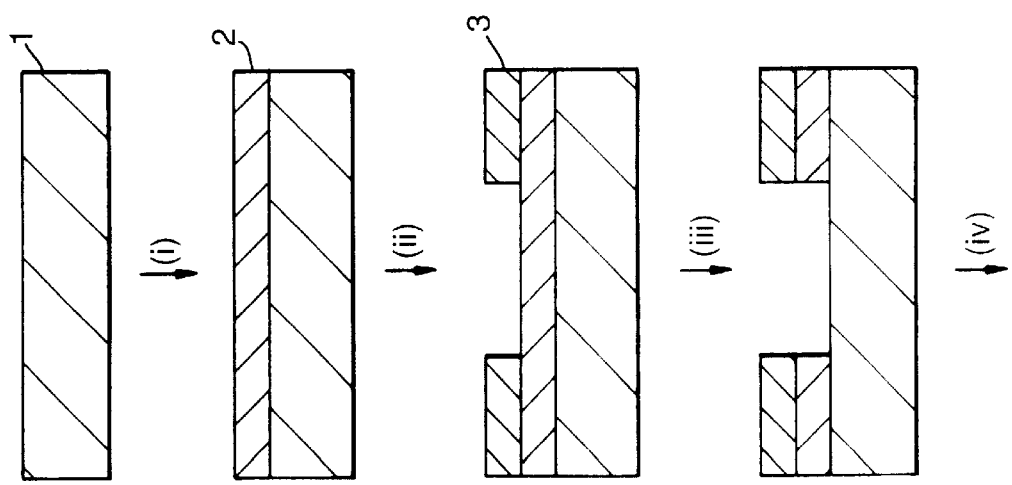

Fig.2.
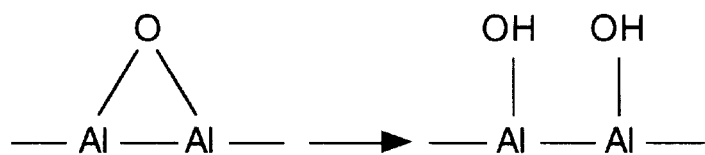
Fig.3.
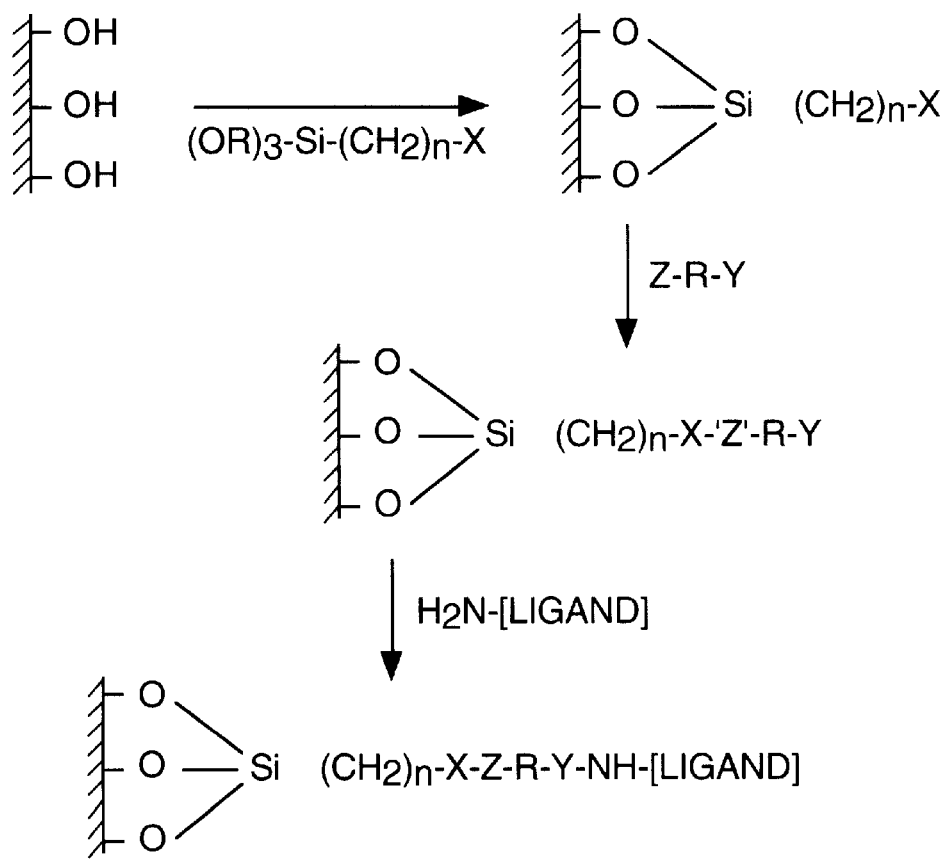

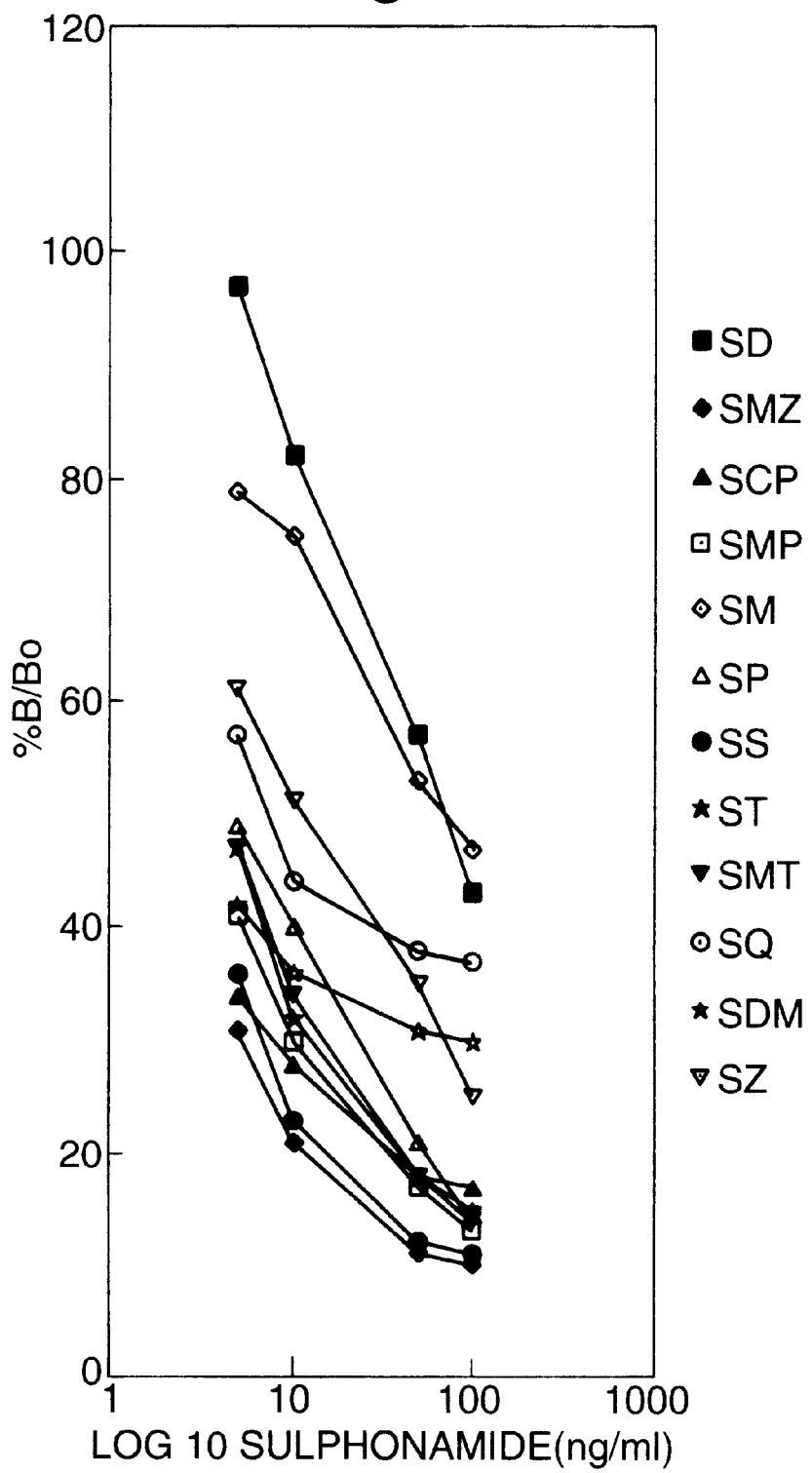

METHOD FOR MAKING A DEVICE FOR THE SIMULTANEOUS DETECTION OF MULTIPLE ANALYTES

This is a division of application Ser. No. 09/061,171 filed Apr. 16. 1998. The entire disclosure of the prior application is hereby incorporated by reference herein in its entirety.

FIELD OF THE INVENTION

This invention relates to a device and apparatus for the simultaneous detection of multiple analytes.

BACKGROUND OF THE INVENTION

Traditionally, structurally-diverse analytes have been analysed by means of specific methods, e.g., enzyme immunoassay, high performance liquid chromatography, gas chromatography, enzymatic methods and colorimetric methods. These methods are predominantly one-analyte, one-test methods.

Automation of analytical methods has generally focused on batch and random access analysers, where multiple analysis on individual test samples is performed using sequential individual test methods. This necessitates the use of multiple packs of individual test kits. In addition, analysis requires employment of several types of equipment, e.g. clinical chemistry analysers, HPLC, GCMS, automated immunoassay instruments or atomic absorption instruments.

A multi-analyte system should involve a means of providing simultaneous analysis of several analytes in a test sample. This analysis should provide results which identify individual analytes and enable the quantitation of each individual analyte in that test sample. A method of multi-analyte analysis is often claimed but the given criteria are generally not both fulfilled.

In a multi-analyte system, a typical substrate contains a plurality of individual test reaction sites each possessing a different binding ligand. The test sample contacts each of the reaction zones and thereafter a range of detection techniques is implemented to identify the analyte present. It is important that the detection method used enables quantitation of each individual analyte.

In order to produce multi-analyte arrays of spatially-distinct areas of biologically-active ligands on a substrate, the most common approach has been through photolithographic techniques. The substrate is coated with a photolabile linker. In theory, this linker should only become reactive towards a binding ligand following irradiation with light of a suitable wavelength. Spatial resolution is achieved by placing a physical mask (normally manufactured from chrome) on the substrate. The pattern of holes in the mask determines the pattern of binding regions on the substrate.

For each biological ligand to be immobilised, the general protocol is: irradiation of first sites, incubation of irradiated substrate with a first ligand to be immobilised, washing to remove loosely bound ligand, blocking unreacted sites activated by the irradiation step, and irradiation of regions where the second biological ligand is to be immobilised, with subsequent steps repeated as for the first ligand. The spatial resolution is dictated by controlling the site of irradiation, either by controlling the site of irradiation by means of a coherent UV light source from a laser or by a number of physical masks and an incoherent light source. This makes the task of immobilising a plurality of biological ligands a time-consuming process. Another disadvantage of the photolithographic approach is the need for expensive physical masks or a laser light source. Further, there is a high degree of non-specific binding.

For example, the use of arylazides, fluoro-arylazides and benzophenones has been associated with a high degree of non-specific binding. High non-specific binding results in assay background being high, significantly reducing the dynamic range of each multi-analyte assay. The non-specific binding is largely due to passive adsorption of molecules to the non-activated photolabile linker surface through ionic interactions, Van der Waals forces etc.

WO-A-9516204 describes a photolithographic approach to reducing the problems associated with high non-specific binding. In this approach, the surface linking molecule was avidin and the photolabile molecule was photobiotin or a derivative thereof. Whilst reduced non-specific binding is claimed, this technique still requires the time-consuming sequences outlined above. Immobilisation of a plurality of 20 separate biological ligands would require a total of 80 steps, assuming the basic requirement of irradiation, binding, blocking and washing steps for each separate ligand to be immobilised.

Spatial resolution has also been achieved by passive adsorption. For example, U.S. Pat. No. 5,432,099 discloses binding whereby the ligand to the substrate surface through a combination of ionic interactions, hydrophobic interactions, and Van der Waals forces.

Passive adsorption processes are dependent on changes in pH, temperature, ionic strength and on the type of substrate used, making the binding process more difficult to control.

The major drawback with this approach is the susceptibility of a proportion of weakly immobilised ligand to be desorbed during the washing step or incubation steps of the biological assay, resulting in poor intra and inter-assay precision.

A cross-linker used in many publications has been glutaraldehyde. This linker presents many disadvantages, including the tendency of proteins to cross-link which is likely to alter the function of the protein. A further disadvantage is that the coupling procedure should include a reduction step which is time-consuming and potentially very hazardous, e.g. if sodium cyanoborohydride is used as the reducing agent.

Heterobifunctional linkers have been used but in many cases these involve the need for free sulphydryl groups on the protein to be bound. This necessitates modification of the protein prior to immobilisation.

In a multi-analyte assay, it is desirable to provide both qualitative and quantitative results. Multi-analyte assays have been available for antibiotics, for example. These are largely based on microbial inhibition assays, where an antibiotic present in the sample inhibits bacterial growth and forms a zone of clearance which is proportional to the concentration of the antibiotic present in the sample. However, this method cannot provide any indication as to the identity of the antibiotic, or an accurate determination of its concentration. Microbial inhibition methods are also very slow, the complete process taking several days.

Chemical screening methods such as high performance liquid chromatography (HPLC) or gas/liquid chromatography mass spectrometry (GCMS/LCMS) struggle to accommodate the structural diversity/polarity extremes of each antibiotic group, e.g., penicillins, sulphonamides, aminoglycosides, tetracyclines etc. In addition, chromatographic methods necessitate extensive sample preparation in order that the signal-to-noise ratios are such that the required detection limits can be achieved.

Available multi-analyte devices include the Triage (see Clinical Chemistry 38(9):1678–1684 (1992)) and Advisor (see Clinical Chemistry 39(9):1899–1903 (1993)). These devices are only suitable for qualitative analysis.

The Triage device is for the simultaneous detection of a panel of seven drugs of abuse in human urine. Each device is only capable of analysing one urine sample. At the end of the procedure, the operator visually examines each of the drug-specific test zones for the presence of a red bar. All steps of the assay protocol must be performed manually by the operator. There is also no hard-copy of the test result available.

The Advisor device is similar in its application to that of the Triage device. The Advisor device screens for five different classes of drugs of abuse. The device operates using agglutination assay principles, with individual channels for each drug. All steps of the assay protocol are performed by the operator. Negative samples have agglutinated particles, whereas positive drug samples provide an unaggregated pattern of particles.

The majority of biosensors/microfabricated devices for biological application have employed silicon as the substrate. Others use glass or quartz substrates. Silicon has a very controlled crystallographic structure with well-defined crystal planes. The uniformity of the silicon substrate makes it an ideal choice for the development of a multi-analyte test device.

However, dark substrates such as silicon give so-called black body effects. In the case of detection by fluorescence, in which a fluorophore is excited using light of a particular wavelength, a dark substrate may absorb the incident excitation light energy, thus diminishing light emission from the fluorophore.

SUMMARY OF THE INVENTION

According to the present invention, a device for performing multi-analyte assays, comprises a substrate and a multiplicity of discrete reaction sites each bearing a ligand covalently bound to the substrate, and in which the surface of the substrate between the reaction sites is inert with respect to analyte. This invention thus provides a solid state, multi-analyte device which exhibits little or no non-specific binding.

A device of the invention may be prepared by activating the surface of a suitable substrate, and applying an array of ligands on to discrete sites on the surface. If desired, the other active areas may be blocked. The ligands may be applied in an aqueous system, and it is preferred if the other areas are rendered hydrophobic. The ligands may be bound to the substrate via a linker. In particular, it is preferred that the activated surface is reacted successively with an organosilane, a bifunctional linker and the ligand.

As part of this invention, bifunctional cross-linkers have been used to provide highly efficient coupling chemistries between organosilanes covalently immobilised on microfabricated silicon or ceramic substrates. Biological ligands can thus be immobilised in multi-analyte arrays.

This invention removes the need for multiple individual test reagent kits and also several instrument types, thereby facilitating the simultaneous detection of multiple analyses on a single sample. The invention provides a single integrated analyser capable of providing simultaneous detection of a wide range of chemistries. In addition, test reagents may be supplied in a combined format for a particular panel of analytes.

As part of this invention, a plurality of biological ligands is immobilised in a spatially-defined pattern of spots or lines by means of microfluidic dispensing of the ligand onto a chemically-activated substrate. The biological ligand is covalently attached to the substrate. The coupling efficiency of the biological ligand can be such that the chemical reaction is completed within a few minutes. The immobilisation procedure can ensure that the biological ligand retains its biological activity both in the short term and in the long term.

This invention also provides an integrated analyser system for the simultaneous detection of a wide range of analytes in a multi-analyte format. The analyser system is designed for maximum end-user convenience, with the capability of obtaining multi-analyte identification and quantitation from each test sample. The preferred analyser system is a combination of a X-Y translational platform, a sample handling unit, liquid handling/flow control means, a temperature-controlled dark box, a CCD camera, and image-processing software. The platform may be associated with a stepper motor, to achieve a positioned accuracy of, say, 10 $\mu$m, for positioning device(s) at each stage of the analytical procedure.

DESCRIPTION OF THE DRAWINGS

In the accompanying drawings:

FIG. 1 shows the formation of a non-uniform substrate surface;

FIG. 2 shows the chemical activation of groups on the surface of a substrate;

FIGS. 3, 5 and 6 show the covalent immobilisation of a ligand at the surface of a substrate;

FIG. 15 shows calibration curves for analytes assayed by means of the invention.

DESCRIPTION OF THE INVENTION

Figure 4:
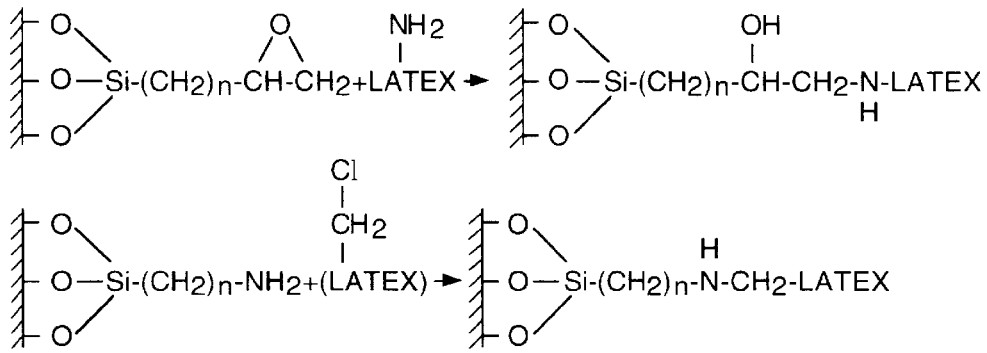
FIG. 4 shows the use of latex particles at the surface of a substrate.

The substrate that is used in a device of this invention may be, for example, of silicon, quartz, glass or ceramic. Ceramic substrates (aluminium oxide) provide an excellent alternative to silicon substrates, since both fluorescent and chemiluminescent detection techniques can be employed successfully. These findings were unexpected, since the crystallography of ceramic materials would not make them an immediate substrate choice.

A ceramic substrate may be manufactured to provide a range of grain sizes (1 to 30 $\mu$m). The preferred particle size of the ceramic substrate used in this invention is less than 20 $\mu$m, preferably less than 10 $\mu$m. The reduced particle size imparts much improved surface uniformity which in turn provides enhanced performance of biological assays. Other important features of ceramic substrates include surface topography tolerance, porosity, vacuum-tightness and zero absorption of water.

The preferred ceramic material consists of 94% alumina ($Al_2O_3$) with a particle size in the range of 4–8 $\mu$m. The material is vacuum-tight, and has a surface topography of 0.6 to 0.8 $\mu$m when ground. The surface uniformity can be improved by a polishing process, to yield a surface with variation of 0.4–0.5 $\mu$m. A further improvement is achieved by lapping and polishing, to yield a surface with a variability of 0.05–0.1 $\mu$m.

The performance of certain ceramic substrates has been found to be dependent on the characteristics of the grain size. The superior assay performance was found for ceramic materials having a grain size of up to 8 μm, e.g. 4–8 μm. Results for materials of higher grain size were not found to be so satisfactory. Ceramic substrates with grain sizes of approximately 1 μm were evaluated and did not give improved results, with respect to those achieved for the 4–8 μm substrate. This is advantageous, since the material cost is considerably higher (approx. 5-fold) for the very small particle ceramic.

Suitable silicon substrates are produced with an oxide film of an exact thickness, e.g. a tolerance of ±2 nm for a 100 nm oxide film. The oxide film may be 50–500 nm thick, preferably less than 200 nm, more preferably in the region of 100 nm.

The substrate may be formed as part of a solid-state microfabricated micromachined device, developed for a wide range of panel tests for veterinary and clinical diagnostics applications. Each solid-state test device has an array of reaction regions.

Each reaction region is specific for an individual analyte. The reaction region may be in the form of a spot, channel, dimple, pit, well or chamber. The reaction regions are manufactured by immobilising biological molecules onto the substrate. Typically, a device of the invention is up to 1 $cm^2$ in area. The area of each reaction site will usually be less than 1 $mm^2$.

The solid substrate is preferably fabricated to provide an intricate network of ports, chambers, channels, wells, dimples etc. It may also be advantageous to create pillars within the channel or well. Such irregularities can help to achieve maximum surface area interactions between bound biological ligands and test reagents, greatly reducing the incubation times for competitive immunoassays and sandwich immunoassays alike.

As an alternative or in addition to, say, dimples or channels on the silicon or ceramic substrate, the surface may also be microfabricated to incorporate nanoliter to microliter mixing chambers/reservoirs/channels. For example, the silicon surface is first oxidised to form an oxide layer. A layer of photoresist is then deposited from which the desired pattern is created. After formation of the pattern on the oxide layer, the photoresist is removed. The silicon is then etched, e.g. using HF, and oxide film removed. Finally, the oxide film is grown uniformly over the entire silicon wafer.

An illustrative process is shown in FIG. 1. In step (i), a silicon wafer 1 is oxidised to provide an oxide layer 2; in step (ii), a photoresist layer 3 is deposited; in step (iii), the application of light provides a patterned oxide layer; in step (iv), the photoresist is removed;

in step (v), the wafer 1 is etched; in step (vi), the oxide film is removed; and in step (vii), a continuous oxide film 2a is reformed.

Covalent immobilisation of the biological ligands is preferred. Passive adsorption interactions may be used, but are susceptible to changes in pH, temperature and ionic strength, and may in some instances result in release of weakly-bound ligands during incubation and washing steps, thus contributing to poor assay reproducibility. It is of course desirable that the biological ligand retains maximum activity, after the immobilisation procedure.

Prior to any chemical activation, the surface of the substrates should be thoroughly cleaned. The first step preferably involves cleaning of the surface by sonication in an alkaline detergent, followed by exhaustive washing with double-deionised water. The substrates are then treated with a chromic acid solution. The chromic acid solution both further cleans the surface and opens surface epoxide groups, as shown in FIG. 2. The epoxide groups may also be opened by other means, e.g. sonication for 1 hour.

The surface hydroxyl groups thus formed are then available for derivatisation. For example, as shown in FIG. 3, a sequence of reactions comprises the use of an organosilane, then a (hetero)bifunctional cross-linker Z-R-Y, to form a highly reactive intermediate, and finally a functionalised ligand, to give covalent immobilisation.

In more detail, in the organosilanes of the formula $(RO)_3Si-(CH_2)_n-X$, each R is an alkyl or other hydrocarbyl group such as $CH_3$ or $CH_2CH_3$; n is an integer, e.g. 1 to 18; and X is a functional group such as epoxycyclohexyl, $NH_2$, CHO, OH, SH, p-chlorobenzyl, m-chlorobenzyl, Br, Cl, $-NH-CH_2-CH_2-NH_2$, 2,3-epoxypropoxy, $-N=C=O$, $-N=C=S$ or p-chlorosulphonylphenyl. These organosilanes may be chosen to provide either a reactive terminal group, capable of forming a covalent bond with a biological molecule, or a less reactive moiety such as $NH_2$ where further activation with a bifunctional linker is necessary to provide an appropriate end group. Organosilanes possessing terminal electrophilic functional groups do not require activation with a bifunctional cross-linker, since biological ligands can be immobilised covalently through nucleophilic groups on the biological ligand.

In the case of organosilanes possessing nucleophilic groups, any of a multitude of bifunctional cross-linkers may then be used to provide a very reactive chemical group through which a biological molecule or ligand can be covalently attached. This invention includes the use of bifunctional linkers which can be used in the mass production of chemically-activated substrates and are sufficiently stable to permit long-term storage prior to covalent attachment of the biological molecule or binder ligand. Preferred linkers are inert to normal atmospheric conditions whilst also being sufficiently reactive to form covalent bonds with functional groups of the biological ligand to be immobilised in a very short time period (typically <10 minutes).

The bifunctional linker may be, for example, phosgene, thiophosgene, N,N-disuccinimidyl carbonate, xylylenediamine, 1,6-diaminohexane, 1,12-diaminododecane, 1,6-diisocyanatohexane, 1,12-diisocyanatododecane, 1,4-phenylenedithioisocyanate, cyanuric chloride, terephthaldehyde, p-nitrobenzoyl chloride, sulfanilic acid, 2-fluoromethylpyridinium p-toluenesulfonate, 3-aminophenylboronic acid, p-bromophenylboronic acid, diethyl pyrocarbonate, ethyl chloroformate, p-bromoaniline, p-bromophenyl hydrazide, p-bromobenzaldehyde, the 1,2-ethylene glycol of p-bromobenzaldehyde, N,N'-carbonyldiimidazole, terephthaloyl chloride, epichlorohydrin, 1,4-diiodobenzene, 1,4-dibromobenzene or a N-hydroxysuccinimide derivative, e.g. of p-aminobenzoic acid, p-bromobenzoic acid, p-bromophenylacetic acid, p-bromoethylbenzoic acid, p-bromomethylbenzoic acid, p-formylbenzoic acid, p-hydroxymethylbenzoic acid, 1,2-ethylene glycol of p-formylbenzoic acid, p-bromophenylpropionic acid or p-hydroxyphenylpropionic acid. A photolabile cross-linker may be used to react with an organosilane having a nucleophilic or electrophilic terminal group. The cross-linker is, for example, the N-hydroxysuccinimide of p-azidobenzoic acid or p-aminobenzophenone.

Instead of, or in addition to, the use of bifunctional linkers, it is also advantageous to covalently immobilise a layer of latex particles. The diameter of the latex particles is preferably less than 500 nm, and more preferably less than 150 nm. The latex particles may have range of functional groups, e.g. —$CH_2Cl$, —CHO, p-chlorophenyl, p-chlorostyryl, —N═NH, —NH—$NH_2$ or —$NH_2$. The latex particles may be incubated at a concentration of approximately 0.5 to 1% w/v with substrates modified with the appropriate organosilane, with or without the presence of a bifunctional linker as described above.

FIG. 4 shows two reaction schemes for the immobilisation of latex. Either may be followed by activation of the latex with a second linker, and immobilisation of a biological molecule, or direct covalent immobilisation of, say, an antibody.

Figure 5:
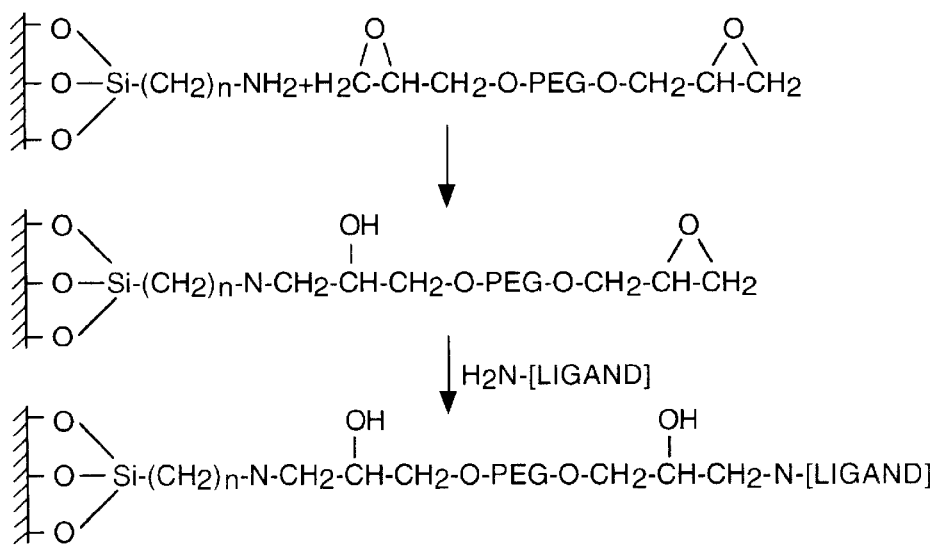

An alternative to the use of polystyrene latex particles is the covalent immobilisation of biological ligands to polyethylene glycol derivatives already anchored on a silanated substrate. For example, PEG derivatives with two electrophilic groups such as epoxy or carbonylimidazole are reacted with a silane having a terminal —$NH_2$ group, such as APTES, on a substrate of choice. A suitable reaction sequence is shown in FIG. 5.

Figure 6:
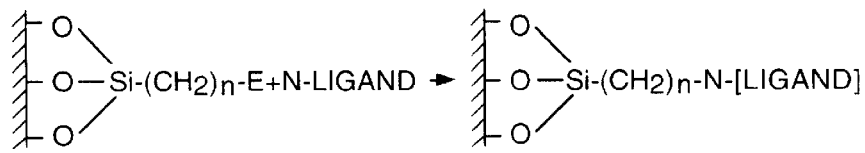

It may also be advantageous to covalently immobilise the biological ligand directly to the silane layer, thus avoiding the need for activation of the silane with polymeric materials or bifunctional linkers. The organosilanes should be receptive to nucleophilic attack by a chemical group (e.g. $NH_2$, SH, OH or NH═$NH_2$) on the biological ligand. Organosilanes that are suitable for direct biological ligand attachment may possess halide, epoxy, isocyanato, aldehyde or tosylate functional groups. Such as reaction is shown in FIG. 6, wherein E is an electrophilic group on the organosilane. Examples of E are Br, Cl, —O—$CH_2$—CH═$CH_2$, —NCO, —CHO and p-chlorosulphonylphenyl.

Organosilanes possessing electrophilic groups, e.g., glycidoxy, also have the advantage of being less susceptible to polymerisation during the silanation procedure due to the absence of nucleophilic groups available for attacking the methoxy or ethoxy function of the organosilane. Therefore, the substrate surface should not contain polymerised organosilane.

The chemistry of the surfaces provides a means of achieving spatial resolution by virtue of the rapid kinetics of the formation of covalent bonds between the surface chemical functional group and a suitable chemical group present in a sterically favourable position on the biological molecule to be immobilised. The biological molecule is preferably presented to the surface of the substrate by a microfluidic dispenser in the form of an individual droplet or series of droplets which form a line. The volume dispensed is of the order of 1 to 100 nl, preferably less than 50 nl, e.g. closer to 10 nl. The rapidity of the formation of the covalent bonds is such that covalent immobilisation is achieved in minutes, before the dispensed droplet or line evaporates on the surface. The positional accuracy to which the droplet or line of liquid is delivered should have a tolerance of ±20 μm.

Especially if ligands are applied in water, it is also desirable to develop a surface which is hydrophobic, to prevent any lateral diffusion of the dispensed droplet or line. This property contributes to excellent spot quality and reproducibility and enables a greater number of spots of biological molecules to be covalently immobilised per unit surface area.

The present invention overcomes the problems associated with conventional photolithography, by enabling the formation of spatially distinct spots of biological ligands, with no requirement for UV light or physical masks. As indicated above, spatial resolution may be achieved by microdispensing techniques. An important factor is the rapid kinetics of the covalent coupling reaction, to ensure highly efficient coupling of the biological ligand in a spatially distinct region, eliminating the lateral digression of the immobilised biological ligand.

Unreacted chemical moieties on the substrate may then be blocked, e.g. using blocking molecules known to those skilled in the art. Suitable such molecules include proteins such as casein, bovine serum albumin, lactalbumin etc. or low molecular weight blockers such as glycine, glutamine etc.

Photolabile linkers can also be used. For example, the organosilane on the surface of the substrate is reacted in the dark with a photolabile linker (e.g. benzophenone, arylazides etc.) The surface is then spotted with the biological ligands as desired, and covalent attachment is achieved following a short period of irradiation with UV light or a longer period with visible light. The remaining regions of the substrate surface are blocked, using blockers similar to those described molecules as above, in the presence of UV or visible light.

The substrate-immobilised biological molecules may be stabilised, e.g. by incubation in a sugar solution (e.g. trehalose) for a short time (1 hour), followed by drying at 37° C. for 16 hours. The stabilised substrates may then be sealed in foil pouches with desiccant and stored. The immobilised biological molecules are stable for more than 6 or 12 months, e.g. up to and beyond 2 years when stored at +2 to +8° C.

The devices may be placed in a range of different carriers which incorporate features which control the efficiency of mixing of test reagents. The flow of liquid test reagents may be achieved by capillary attraction, centrifugal force, vacuum force or electroosmotic flow. The use of electroosmotic flow may avoid the need for valves, so that no moving mechanical parts are used.

Closed channels may be formed by bonding a glass plate to the microfabricated surface. The biological molecules are covalently immobilised on the surface prior to bonding the glass plate. Many bonding procedures, e.g. anodic bonding, involve elevated temperatures that may destroy a biological molecule. Therefore, bonding techniques should be nondenaturing, to immobilised biological molecules. One suitable method is indirect bonding, e.g. where the wafer is bonded to a glass plate by a suitable glue, e.g. epoxy glue.

Figure 7:
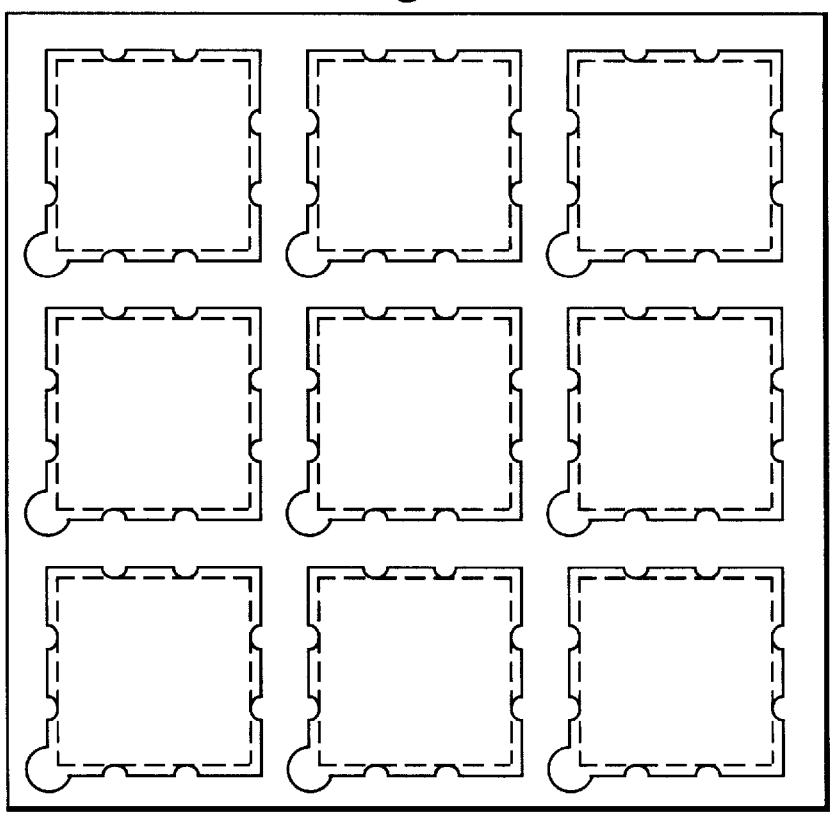
FIGS. 7–11 illustrate devices for the incorporation of chips embodying the invention.
Figure 8:
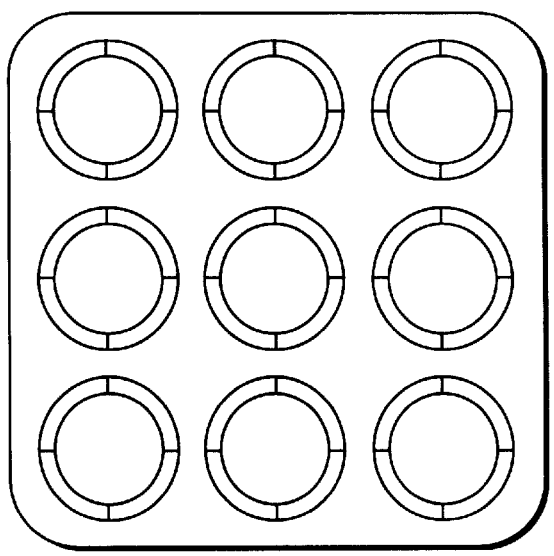

The devices may then be placed in a suitable carrier. Various such carriers are illustrated in FIGS. 7 and 8. By way of example, the dimensions of the device shown in FIG. 8 are 48.62 mm×48.62 mm, including wells having an internal diameter of 10 mm and an external diameter of 12.82 mm. The centre-to-centre spacing of the wells is 15.36 mm.

Figure 9:
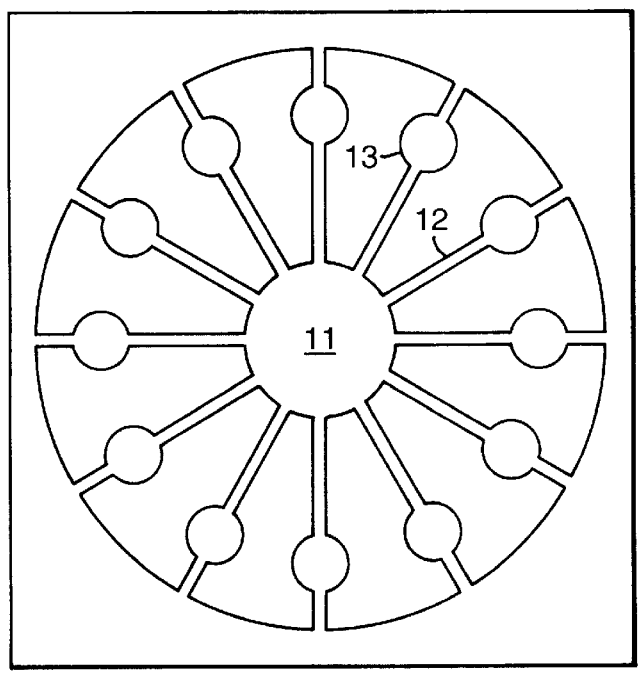

The devices may incorporate features to enhance mixing of test reagents, samples etc. This is illustrated in FIG. 9, where the device includes a reagent addition site 11, reagent channels 12, and test reaction sites 13.

Figure 10:
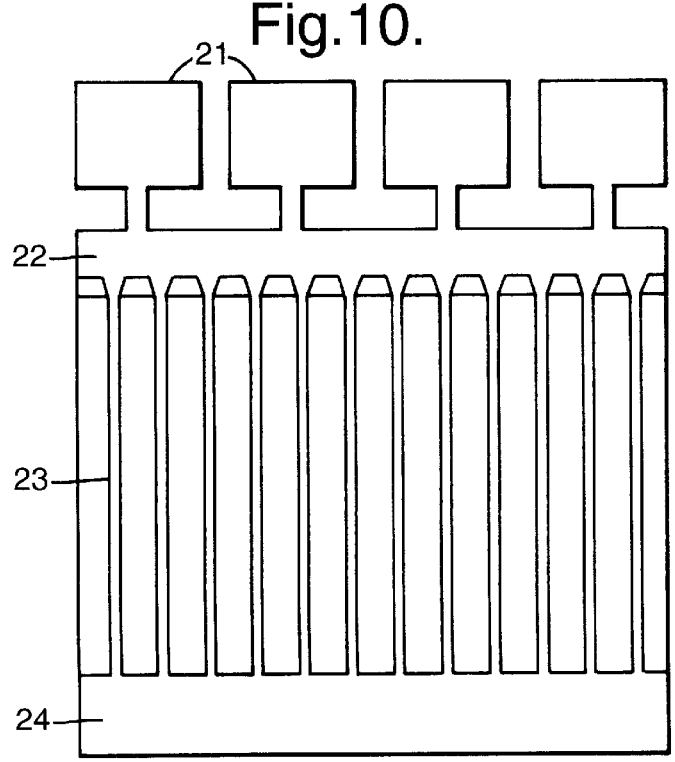
Figure 11:
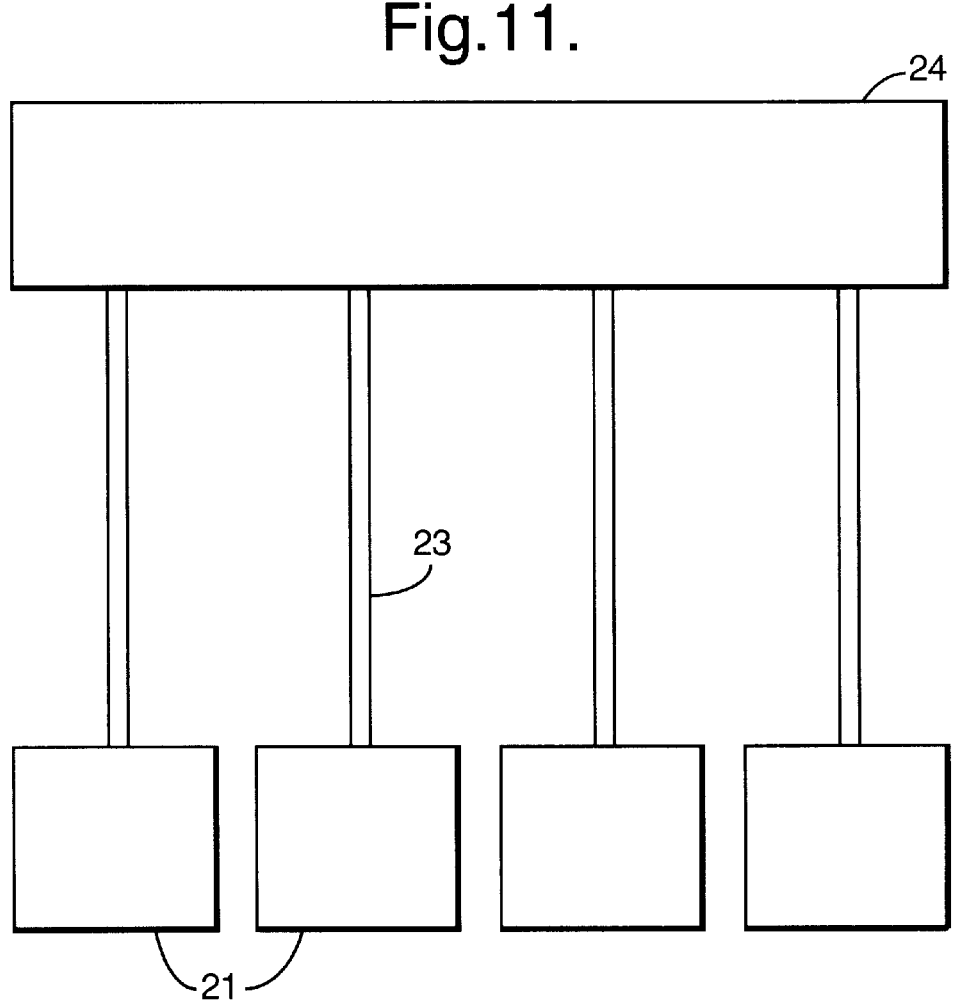

In FIG. 10, the device includes reagent reservoirs 21, a delivery manifold 22, reagent delivery channel test sites 23, and a waste reservoir 24. FIG. 11 shows a 4-channel test structure with similar parts.

This invention provides a completely integrated system for the simultaneous, quantitative detection of analytes of a wide range of molecular weights, structural diversity and polarity. Analyte panels are available as appropriate for clinical/veterinary diagnosis or drug screening.

Depending on the analytes, binding ligands are chosen accordingly. This is within the skill and knowledge of those in the art. Suitable analytes include:

- antibiotics, e.g., tetracyclines, sulphonamides, ionophores, aminoglycosides, penicillins or fluoroquinolones;
- hormones, e.g. Luteinising Hormone (LH), Prolactin (PL), Follicle Stimulating Hormone (FSH) or Thyroid Stimulating Hormone (TSH);
- markers of cardiac damage, e.g., myoglobin, carbonic anhydrase, troponin I, glycogen phosphorylase BB, CK-MB, fatty acid binding protein or troponin T;
- markers of infectious disease;
- allergy markers;
- drugs of abuse;
- enzymes;
- viruses;
- nucleotides; and
- peptides.

For example, one panel is for the detection of sulphonamide antibiotics. This invention provides a method for the simultaneous quantitative identification of, say, up to individual sulphonamides. Other examples include cardiac, fertility and infectious disease panels.

The invention makes it possible to simultaneously detect up to, say, 20 analytes which may have no structural similarity. Sample matrices that may be tested include serum, plasma, urine, bile, faeces, tissue, water and feed. The volume of sample required is very low, typically <1.5 $\mu$l/analyte. The test reagents, e.g. enzyme-labelled antibodies, enzyme-labelled haptens, fluorescently-labelled antibodies or fluorescently-labelled haptens, may be all contained in a single reagent reservoir, dramatically reducing the liquid-handling requirements.

In sandwich assays, e.g. of Luteinising Hormone, Follicle-Stimulating Hormone, prolactin, Thyroid-Stimulating Hormone etc., the sample is added along with an assay buffer and incubated for a short period which is typically less than 30, and preferably less than 10, minutes. Following a wash step, the cocktail of labelled detecting antibodies is added and incubated for a further period of time. This period is again typically less than 30, and preferably less than 10, minutes. The device is then washed, to remove any unbound label, and the signal quantified.

It may be advantageous for certain assays to incorporate a facility within the microfabricated device to remove potential interferents such as rheumatoid factor interference. Removal of rheumatoid factor may be achieved by contacting the test sample to an area of immobilised immunoglobulin, for example prior to the test sample contacting the reaction region.

A further example is HAMA (Human Anti-Mouse Antibodies) interference; these antibodies can cause severe problems in the performance of assays utilising monoclonal mouse antibodies. The traditional solution is to include expensive additives in test reagents to counteract the problem. In this invention, there is the advantage of removing the HAMA interference by contacting the sample with regions on the microfabricated device, to remove these antibodies, prior to the sample reaching the reaction region.

More generally, ligands may be provided over part of the device, that bind contaminants. This is especially valuable where defined spreading is allowed on the surface of the device, e.g. in channels. The capability of removing components that interfere enhances the accuracy of the results generated.

The detection labels may also be immobilised on the surface of dendrimer molecules. The dendrimer molecules are polymeric in nature, synthesised by the repetitive coupling of small building molecules. They are commercially available from Aldrich Chemicals in a range of molecular weights with a choice of terminal functional groups e.g. $NH_2$ or COOH. Heterobifunctional linkers can then be used in conjunction with conventional coupling chemistry to prepare the detecting label conjugates. For small hapten molecules, e.g. $\beta$-agonists, anabolic steroids or antibiotics, it is preferred that a small dendrimer preferably no more than 16 surface groups) is coupled to a large dendrimer (typically more than 64 surface groups). The small molecular weight hapten (less than 1,000 Dalton) is coupled to the chemical groups on the small dendrimer followed by covalent attachment of the detecting label. The dendrimer conjugate may be purified by dialysis and gel permeation chromatography.

The test reagents contain multiple components (e.g. enzyme-labelled antibodies, fluorescent-labelled antibodies, latex-immobilised antibodies, dendrimer antibody-fluorophore conjugates, dendrimer antibody-fluorophore conjugates, dendrimer antibody-enzyme conjugates, enzyme-labelled haptens, fluorescent-labelled haptens, etc.) as appropriate for particular panels of tests. The panels of tests possible are very diverse and can be chosen on the basis of clinical diagnosis (or veterinary diagnosis) as appropriate.

For example, a desirable panel is for the detection of infectious diseases (e.g. hepatitis, HIV, syphilis, etc.). Other panels include fertility hormones, cardiac markers, allergy proteins, etc. As well as clinical parameters, there is also the ability to detect large panels of drug residues.

The present invention permits the identification of individual compounds such as antibiotics. For example, a quantitative result can be obtained for up to 20 antibiotics on a device of surface area of 1 $cm^2$ simultaneously, in a time frame of minutes typically, with a sensitivity superior to that for HPLC/GCMS methods and comparable to that for conventional single parameter enzyme immunoassays. This approach may be easily extended to anabolic steroids, beta-agonists, beta-blockers, pesticides, therapeutic drugs etc.

For analysis, chemiluminescence, bioluminescence or fluorescence may be suitable. The detection system is preferably a charge-coupled device (CCD) camera equipped to measure both fluorescent and chemiluminescent light. Briefly, the CCD camera collects the light signal generated from the test areas on the microfabricated device and converts this into relative light units (RLUs).

Fluorescent-based detection systems may be read directly, using appropriate optical filters for the labelling fluorophore.

A suitable chemiluminescent reagent is luminol, which can be analysed at a wavelength of 433–445 nm. Chemiluminescence may also be observed, based on detecting alkaline phosphatase-labelled biological molecules using 1,2-dioxetane.

To facilitate the detection of analytes, this invention preferably utilises a chemiluminescent detection system, using a CCD. A back-illuminated camera is preferred, to improve the capture efficiency at the wavelength of the light generated by the chemiluminescent light reaction (approximately 433–445 nm in the case of luminol).

Figure 12:
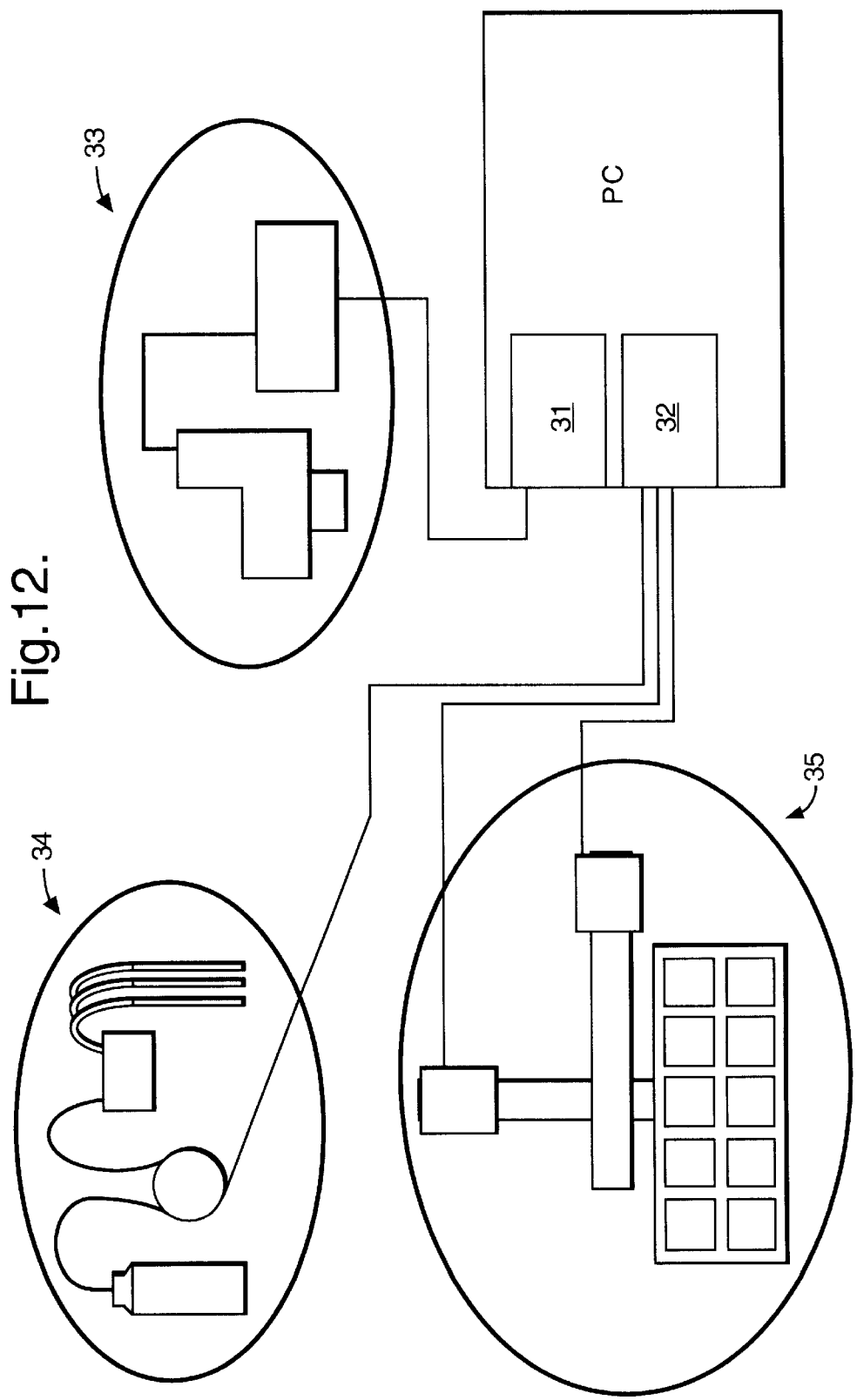
FIGS. 12–14 are schematic views of a system suitable for analysing a device of the invention.
Figure 13:
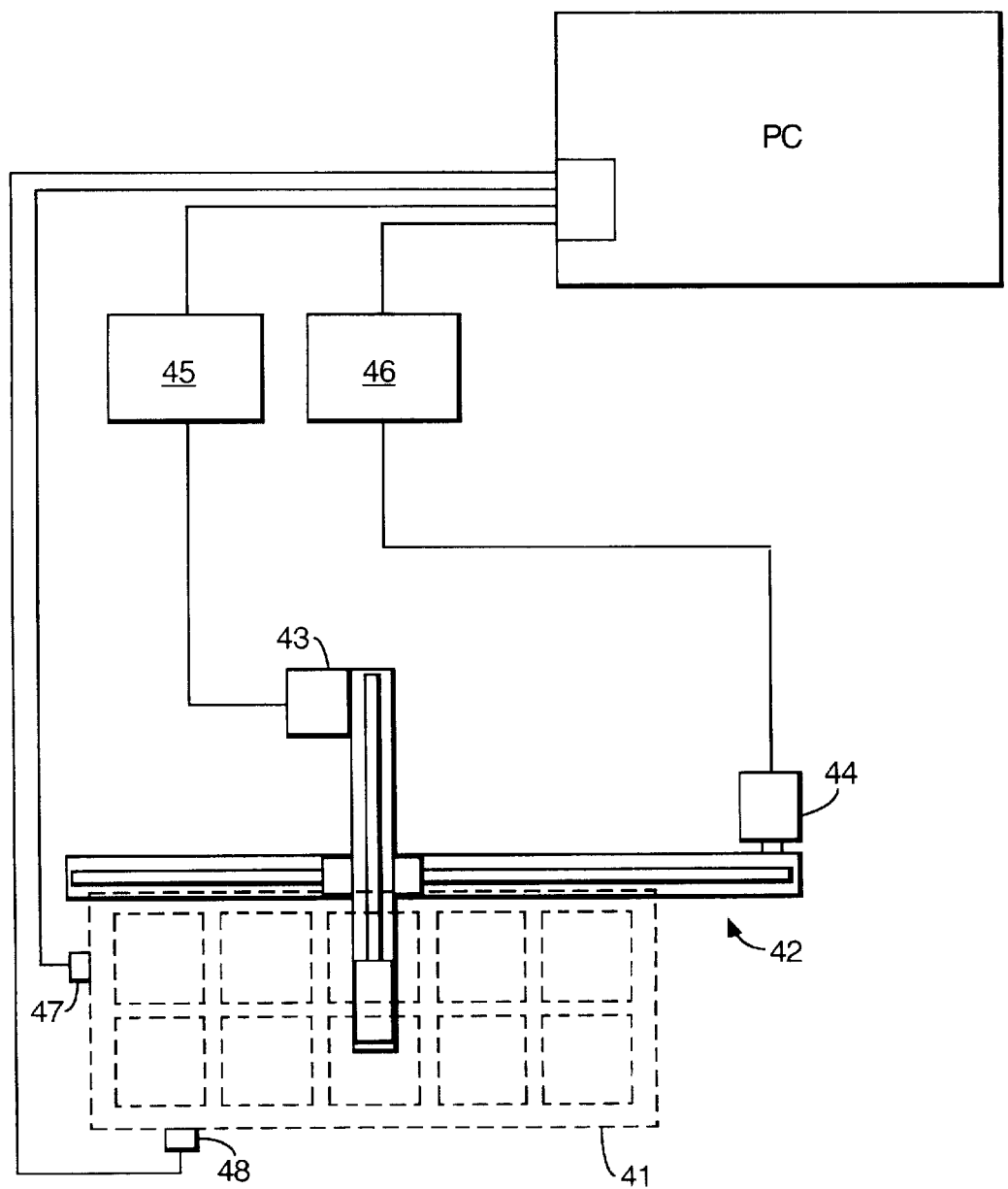

The whole system may be operated by a personal computer where a specifically designed programme controls the X-Y table, dispenser unit, sample handling, temperature control, incubation times and the CCD camera. FIGS. 12–14 show the organisation of such a system.

FIG. 12 illustrates schematically the interaction of a personal computer (PC) having two control units 31,32. Unit 31 is in communication with a CCD imaging system represented at 33. Unit 32 is in communication with a dispenser unit and an X-Y translation table with sample tray represented at 34 and 35, respectively.

FIG. 13 is a schematic representation of the X-Y translation table. This drawing shows a sample translational platform 41 mounted on a linear actuator 42. X-Y translation is under the control of stepper motors 43,44 connected to respective drives 45,46 Translation is limited by "home position" sensors 47,48.

The sensitivity of labelled biological molecules and certain unlabelled biological molecules to light may make it necessary to perform the assays in the absence of light. The absence of light is achieved by constructing the case in a light-tight manner. The light-tight environment is also preferably temperature-controlled, e.g. within ±0.2° C. or, preferably, ±0.1° C., to ensure satisfactory assay precision and accuracy.

Figure 14A:
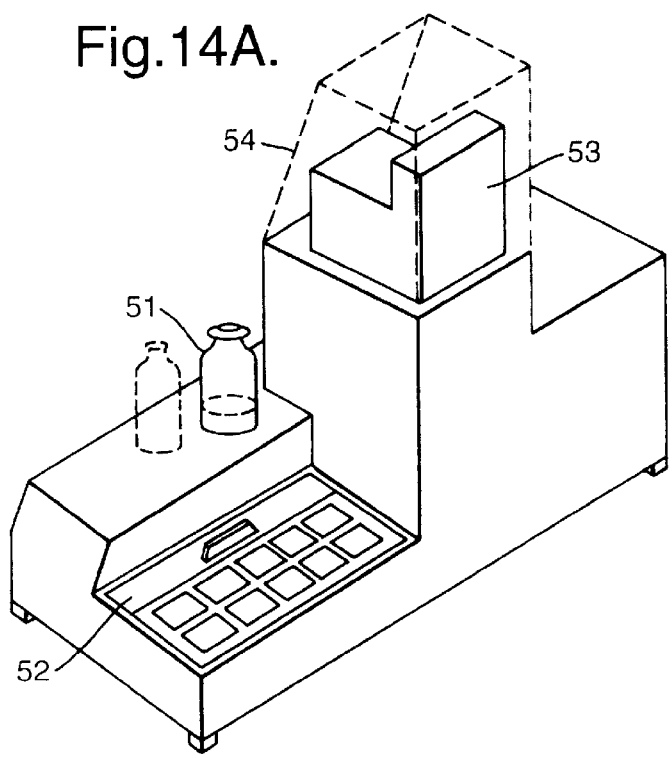

FIG. 14 shows the apparatus in perspective, part plan and cut-away side views. In particular, FIG. 14A shows reagent storage container 51, a light-tight door 52 and a camera body 53 with a removable cover 54. The major part of the camera can be external to the casing. The camera lens is placed in an aperture in the casing.

Figure 14B:
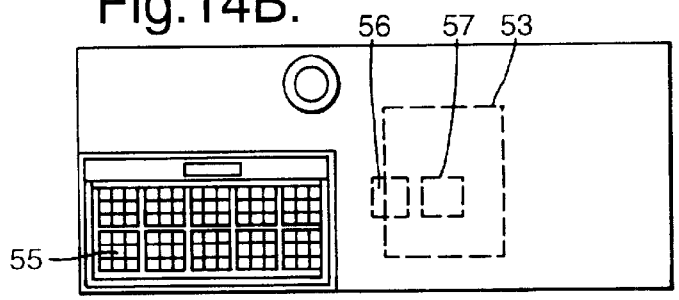
Figure 14C:
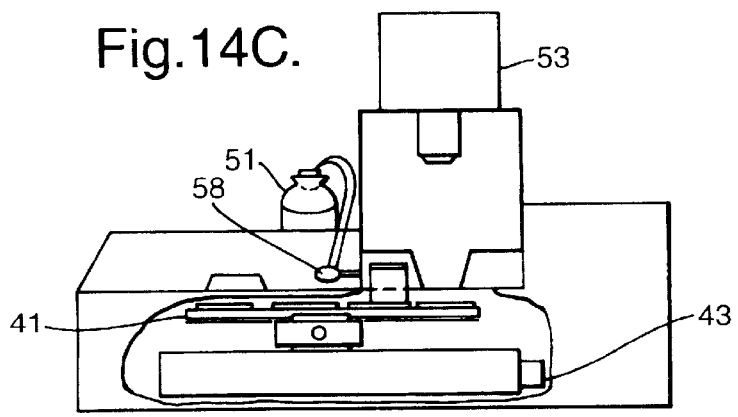

FIG. 14B shows in outline the samples on a sample tray 55 and, in outline, waste area 56 and an imaging area 57. The camera 53 is positioned over these areas. FIG. 14C shows, in addition to the container 51, camera 53, X-Y translational platform 41 and stepper motor 43, a dispenser pump 58.

The design of the system shown in FIG. 14 is based on 3×3 sample rack holders of which 20 can be held at any one time. This means that, if 20 individual reaction regions are located on each 1 cm² of microfabricated device, a total of 3600 analyses may be performed simultaneously on a single sample. Alternatively, 180 samples may be analysed simultaneously for 20 different test parameters.

As indicated above, the analyte may be labelled. The ligand may also be labelled, allowing analysis by fractional occupancy.

The following Examples illustrate the invention.

Example 1

Sulphonamide Assay

In this example, 12 individual antibodies, each antibody specific for a single sulphonamide, were immobilised by covalent attachment by contact interactions on to discrete regions of a flat ceramic (aluminium oxide) substrate having a chemically modified surface. A multi-analyte assay was performed, using a competitive immunoassay format.

In more detail, ceramic substrates (1 cm×1 cm) were ultrasonically cleaned using an alkaline detergent (RBS35, 5% v/v) followed by double deionised water and then placed in 6M HCl for 16 hours. The chips were then placed in chromic acid for 1 hour in an ultrasonic bath.

The substrates were washed exhaustively with double deionised water and acetone and then dried in an oven at 120° C. for 2 hours. Following this pretreatment, the substrates were silanated using the organosilane y-glycidoxypropyl trimethoxysilane (10% v/v) in anhydrous toluene, 4-dimethylaminopyridine (1.25 g/L) and triethylamine (1 % v/v). This mixture was refluxed for 4 hours and then left overnight at room temperature. The substrates were washed with toluene and acetone before curing for 4 hours at 120° C.

Following the curing step, the substrates were placed in containers and stored at room temperature until required for spotting of sulphonamide antibodies. The sulphonamide antibodies were spotted using a BIODOT XY3000 dispenser. The 12 sulphonamides assayed were sulphadoxine, sulphamethizole, sulphachloropyridazine, sulphamethoxypyridazine, sulphamerazine, sulphapyridine, sulphisoxazole, sulphathiazole, sulphamethazine, sulphaquinoxaline, sulphadimethoxine, and sulphadiazine.

Dispensed volumes of approx. 20 nl were employed for each sulphonamide antibody. The 12 sulphonamide antibodies which formed 12 discrete areas on the 1 cm² substrate were incubated for 2 hours at 37° C. The substrates were washed with phosphate-buffered saline (PBS) (pH 7.2) containing 2% casein (w/v) and then blocked in same buffer overnight at +2–8° C. After washing with PBS containing PEG300 (0.05% v/v), the devices were placed in a carrier.

Multi-sulphonamide standards (200 µl) and a cocktail of sulphonamide horseradish peroxidase conjugates (100 µl) were added to the reaction wells containing the device as appropriate and incubated for 15 minutes at room temperature. The standards contained 5, 10, 50 and 100 ng/ml for each of the 12 sulphonamides.

Thereafter the multi-sulphonamide devices were washed with PBS/PEG buffer to remove excess reagents and 300 µl chemiluminescent substrate [luminol (1.4 mM)/urea hydrogen peroxide (9.6 mM)] per device was introduced. The devices were imaged using a CCD camera with an exposure time of up to 4 minutes. Standard curves were obtained for each of the 12 individual sulphonamides. Calibration curves for each of the 12 individual sulphonamides are represented graphically in FIG. 15. The % $B/B_o$ value plotted on the Y-axis represents the % inhibition of the zero standard RLU (Relative light unit) value caused by each individual sulphonamide standard (plotted on the X-axis as $\log_{10}$).

Example 2

Hormone Assay

In this example, a multi-analyte assay was performed for 3 hormones of large molecular weight, i.e. Prolactin (PL), Follicle-Stimulating Hormone (FSH) and Luteinising Hormone (LH). This example represents a multi-analyte assay for a sandwich-based immunoassay. No significant cross-reactivity was observed when the three hormones were determined in the same panel.

The chemical pretreatment and silanation procedures were exactly as described in Example 1. Individual PL, FSH or LH monoclonal antibodies (approx. 20 nl antibody dispensed) were immobilised on discrete areas of the chemically modified substrate. The multi-analyte assays were performed on both silicon and ceramic substrates with an epoxide surface as described in Example 1.

In the assay, 150 µl of a multiple LH/PL/FSH serum-based standard and 150 µl of a diluent assay buffer were added to the device and incubated for 15 minutes at room temperature. Following a wash step, 300 µl of a single conjugate cocktail of LH-HRPO/PL-HRPO/FSH-HRPO conjugates was added and incubated for 15 minutes. Thereafter the devices were washed to remove excess reagents and the chemiluminescent reagent [luminol (1.4 mM)/urea hydrogen peroxide (9.6 mM)] was introduced. The devices were imaged using a CCD camera with an exposure time of up to 4 minutes. Standard curves for each of the hormones were plotted after the images were processed.

Example 3

Sulphonamide Assay

In contrast to Example 1, a multi-sulphonamide assay has also been conducted using microchannels. The device is illustrated in FIG. 11. In this Example, the reagent addition reservoirs 21 are 2 mm×2 mm, and 300 µm deep (vol. 1.2 µl), the channels 23 are each 5 mm long, 200 µm wide and 100 µm deep (vol. 100 µl), and the reservoir 24 is 1.9 mm×8.6 mm, and 300 µm deep (vol. 4.9 µl).

The chemical modification of the surface was performed as described in Example 1. Antibody was added to each of the channels and incubated for 2 hours at 37° C. The substrates were then blocked and washed as for Example 1.

A multi-sulphonamide standard (200 µl) and sulphonamide horseradish pexoxidase conjugates (100 µl) were mixed. 1 µl of the resultant reagent was pipetted into each of the reservoirs supplying the antibody-coated channel for each sulphonamide. The standards contained 10 or 100 ng/ml of all the sulphonamides as appropriate.

The reagent flowed by capillary action. After incubation for 2 minutes, the substrate was washed 5 times with PBS/PEG and chemiluminescent reagent [luminol (1.4 mM)/urea hydrogen peroxide (9.6 mM)] was added.

The devices were imaged using a CCD camera with an exposure time of up to 4 minutes. The % B/Bo values for the 4 sulphonamide curves are given in Table 1.

TABLE 1

| Sulphonamide | % B/B o | | |
|---|---|---|---|
| | 0 ng/ml | 10 ng/ml | 100 ng/ml |
| Sulphamethazine | 100 | 14 | 7 |
| Sulphamethoxypyridazine | 100 | 28 | 15 |
| Sulphaquinoxaline | 100 | 56 | 24 |
| Sulphamerazine | 100 | 40 | 22 |

The utility of this invention by comparison with photolithography was demonstrated by the degree of non-specific adsorption of biological molecules on a photolabile (benzophenone-treated) substrate. The results are shown in Table 2.

TABLE 2

| Mouse IgG | Irradiation By UV lamp (10 minutes) | Grey Mean (RLU) | |
|---|---|---|---|
| ✓ | ✓ | 22368 | 24022 |
| ✓ | X | 17586 | 20531 |

Mouse IgG was detected using anti-mouse HRPO conjugate using chemiluminescent detection by CCD camera. The silicon or ceramic substrates having immobilised benzophenone photolabile linker should not bind mouse IgG when reacted in the absence of light. However, non-specific binding is occurring, since approximately 80% of the grey mean RLU achieved when the mouse IgG binding is performed under UV light is due to passive binding interactions. An array of biological molecules immobilised through covalent interactions according to this invention is demonstrably more distinct.

The evidence for covalent attachment is provided in the examples discussed below. In the first instance, ceramic substrates were silanated with APTES and then reacted with biotin-LC-sulpho NHS. The control ceramic substrate was not silanated with APTES; therefore, no terminal nucleophilic-$NH_2$ groups were available to react with the succinimidyl ester of the biotin derivative. The substrates were then reacted with an avidin-FITC conjugate and the fluorescence determined by CCD camera. Results are given in Table 3.

TABLE 3

| [Biotin-LC-NHS] | APTES Substrate RLU (1 second exposure) | Control Substrate RLU (1 second exposure) |
|---|---|---|
| 0 | 2,448 | NS |
| 100 µg/ml | 8,881 | NS |
| 500 µg/ml | 7,922 | NS |

NS = No fluorescent signal detected.

NS=No fluorescent signal detected.

This clearly demonstrates specific immobilisation of biotin-LC-NHS. The maximum concentration of biotin-LC-NHS immobilised was approximately 100 µg/ml, since the RLU result for the 500 µg/ml substrate did not increase.

In a further example, ceramic substrates silanated with APTES were reacted with a dihydrazide linker. Sulphonamide antibodies were treated with sodium periodate to render them reactive towards the hydrazide linker. Control sulphonamide antibodies were simply dialysed against sodium acetate buffer pH 5.5. The RLU results are shown in Tables 4 (not treated) and 5 (treated by periodate method). The results clearly show that the hydrazide linker has been successfully linked to the ceramic surface. The control antibodies (no periodate activation) gave very poor standard curves when compared to the covalently immobilised sulphonamide antibodies.

The % of binding due to covalent or passive interactions are compared in Tables 6 and 7. Covalent interaction contributed on average 81.8% to the overall binding, clearly indicating covalent binding of the sulphonamide antibodies.

TABLE 4

| SULPHONAMIDE | 0 ng/ml | 10 ng/ml | % B/B$_o$ | 100 ng/ml | % B/B$_o$ |
|---|---|---|---|---|---|
| Sulphadoxine | 2825 | 1456 | 51 | NS | — |
| Sulphamethizole | 3531 | 1257 | 36 | NS | — |
| Sulpachloropyridazine | 6476 | 1585 | 24 | NS | — |
| Sulphamethoxypyridazine | 1099 | 928 | 84 | NS | — |
| Sulphamerazine | 2177 | 1137 | 52 | 1224 | 56 |
| Sulphasoxazole | 4879 | 1108 | 23 | NS | — |
| Sulphathiazole | 2932 | 814 | 28 | NS | — |
| Sulphamethazine | NS | NS | — | NS | — |
| Sulphaquinoxaline | 1041 | 828 | 79 | 968 | 93 |
| Sulphadimethoxine | 804 | NS | — | 781 | 97 |

TABLE 5

| SULPHONAMIDE | 0 ng/ml | 10 ng/ml | % B/B$_o$ | 100 ng/ml | % B/B$_o$ |
|---|---|---|---|---|---|
| Sulphadoxine | 10520 | 3240 | 31 | 2135 | 20 |
| Sulphamethizole | 17141 | 5689 | 33 | 4882 | 28 |
| Sulphachloropyridazine | 24944 | 7565 | 30 | 2096 | 8 |
| Sulphamethoxypyridazine | 14082 | 10509 | 74 | 5687 | 40 |
| Sulphamerazine | 12594 | 5521 | 43 | 3240 | 26 |
| Sulphasoxazole | 24419 | 6686 | 27 | 2270 | 9 |
| Sulphathiazole | 14279 | 4602 | 32 | 2353 | 16 |
| Sulphamethazine | 3644 | 2810 | 77 | 2213 | 61 |
| Sulphaquinoxaline | 10575 | 6112 | 58 | 5588 | 53 |
| Sulphadimethoxine | 5526 | 2554 | 46 | 1983 | 36 |

TABLE 6

| Sulphonamide | Percentage of Sulphonamide Antibody Binding | |
|---|---|---|
| | Covalent Interactions | Passive Interactions |
| Sulphadoxine | 73.1 | 26.9 |
| Sulphamethizole | 79.4 | 20.6 |
| Sulphachloropyridazine | 74.0 | 26.0 |
| Sulphamethoxypyridazine | 92.2 | 7.8 |
| Sulphamerazine | 82.7 | 17.3 |
| Sulphasoxazole | 80.0 | 20.0 |
| Sulphathiazole | 79.4 | 20.6 |
| Sulphamethazine | — | — |
| Sulphaquinoxoline | 90.2 | 9.8 |
| Sulphadimethoxine | 85.4 | 14.6 |
| Mean | 81.8 | 18.2 |

TABLE 7

| | RLU | | | |
|---|---|---|---|---|
| | Covalent | | Passive | |
| Sulphonamide | 0 | 10 ng/ml | 0 | 10 ng/ml |
| Sulphadoxine | 32756 | 11131 | 1950 | 904 |
| Sulphamethizole | 39020 | 11132 | 2782 | 1359 |
| Sulphachloropyridazine | 39632 | 8434 | 4410 | 1051 |
| Sulphamethoxypyridazine | 29489 | 13408 | 1793 | 770 |
| Sulphamerazine | 28455 | 11077 | 2011 | 988 |
| Sulphisoxazole | 38486 | 5774 | 4083 | 1031 |
| Sulphathiazole | 28837 | 8087 | 2010 | 675 |
| Sulphamethazine | 11331 | 7535 | 802 | 574 |
| Sulphaquinoxaline | 13838 | 8716 | 951 | 548 |
| Sulphadimethoxine | 13062 | 5832 | 910 | 581 |

Covalent Immobilisation: Direct spotting on to glycidoxy silane surface.
Passive Immobilisation: Direct spotting on to dichlorodimethylsilane-reacted surface.

Clearly, the covalent method results in superior results compared to the passive method. The results for the passive method can be increased approximately 2-fold by acid pretreatment of the sulphonamide antibodies, but this is still inferior to the covalent approach.

Confirmatory analysis on the chemically-modified silicon and ceramic substrates was also performed using X-ray photon spectroscopy (XPS). Survey spectra were recorded from two random areas of each substrate sample, from which their surface chemical compositions were determined. See Table 8 for results (given in atomic %).

TABLE 8

| Sample | Area | C | O | Si | Al | N | Cl | Ca |
|---|---|---|---|---|---|---|---|---|
| Silicon substrate | 1 | 21.9 | 52.7 | 25.4 | — | — | — | — |
| (untreated) | 2 | 23.0 | 51.0 | 26.0 | — | — | — | — |
| Silicon substrate | 1 | 55.5 | 23.3 | 10.5 | — | 10.2 | 0.5 | — |
| silanated with | 2 | 55.6 | 22.5 | 10.9 | — | 10.5 | 0.5 | — |
| APTES | 1 | 51.3 | 25.6 | 13.0 | — | 7.2 | 2.9 | — |
| | 2 | 52.5 | 25.0 | 12.3 | — | 7.5 | 2.7 | — |
| APTES silicon | 1 | 58.7 | 25.0 | 9.6 | — | 6.1 | 0.5 | — |
| substrate treated with FITC | 2 | 58.8 | 24.7 | 9.8 | — | 6.0 | 0.8 | — |
| Ceramic substrate | 1 | 27.2 | 46.3 | 11.3 | 13.3 | — | 1.4 | 0.5 |
| (untreated) | 2 | 27.1 | 46.6 | 9.6 | 14.8 | — | 1.1 | 0.7 |
| Ceramic substrate | 1 | 47.0 | 31.6 | 13.4 | 2.6 | 5.4 | — | — |
| silanated with APTES | 2 | 45.9 | 31.7 | 13.7 | 3.3 | 5.3 | — | — |
| APTES ceramic | 1 | 52.0 | 29.3 | 11.3 | 2.4 | 5.0 | — | — |

TABLE 8-continued

| Sample | Area | C | O | Si | Al | N | Cl | Ca |
|---|---|---|---|---|---|---|---|---|
| substrate treated with FITC | 2 | 51.0 | 30.6 | 11.7 | 2.3 | 4.5 | — | — |

The atomic composition results show a very good conversion of the parent silicon and ceramic substrates with APTES organosilane, with good reproducibility in surface composition indicated for the two areas tested on each sample. The FITC-labelled substrates showed 70% and 77% labelling of silicon and ceramic respectively.

Quantitative methods of fluorescence measurement on a dark silicon substrate have been compared with those on a white ceramic (aluminium oxide) substrate. The RLU results from CCD detection for fluorescent molecules (FITC) covalently linked to each substrate were compared to the quantitative method after the FITC molecules were stripped by the method of Hook et al (Langmuir 1991, Vol 7, 142–151).

TABLE 9

| Substrate | CCD Exposure Time (sec) | Grey Mean Side 1 | Side 2 | Number of Stripped FITC Molecules/Substrate |
|---|---|---|---|---|
| Ceramic | 0.1 | 7483 | 7063 | $4.548 \times 10^{15}$ |
| Silicon | 10 | 753 | 612 | $1.412 \times 10^{16}$ |

The quantitative analysis of fluorescent label obtained by stripping FITC label from the substrate and measuring the signal by CCD camera shows that, despite the 1000-fold increase in signal of ceramic over silicon, there are actually significantly more FITC molecules present on the silicon substrate.

A further example of this phenomenon is shown by the results in Table 10, from a prolactin assay performed on silicon and ceramic substrates using fluorescent latex particles linked to a prolactin-detecting antibody as the detection system. RLU values are given (20 sec exposure).

TABLE 10

| | RLU | |
|---|---|---|
| [Prolactin] Standard | Silicon Substrate | Ceramic Substrate |
| 550 MIU/ml | 814 | 8594 |
| 2200 MIU/ml | 799 | 16735 |

The performance of ceramic provided superior results to silicon using this fluorescent detection method. Further, the problems of the dark body effect on silicon using fluorescence may be solved by employing chemiluminescence as the detection method. In a comparison between identical assays for FSH performed on silicon and ceramic, using chemiluminescent detection, the former required an exposure time 2-fold longer than that for ceramic to achieve the same RLU value.

| APTES | = | aminopropyltriethoxysilane |
|---|---|---|
| CK-MB | = | creative kinase MB subunit |

-continued

| | | |
|---|---|---|
| HRPO | = | horseradish peroxidase |
| LC-sulfo-NHS | = | long-chain sulfo-N-hydroxysuccinimide |
| FITC | = | fluorescein isothiocarbamate |

What is claimed is:

1. A method for forming a solid state device for performing multi-analyte assays comprising a substrate and a multiplicity of discrete reaction sites each bearing a ligand covalently bonded to a surface of the substrate, wherein areas of the surface of the substrate, which are between the reaction sites, are inert with respect to analyte, said method comprising the steps of:

activating all of said surface of the substrate;

rendering hydrophobic all of said activated surface; and applying an array of ligands onto discrete areas of the hydrophobic surface such that said ligands are not applied to said areas between the reaction sites.

2. The method according to claim 1, wherein said surface of the substrate is non-uniform.

3. The method according to claim 2, wherein said substrate comprises an array of reaction channels, ridges, pillars, spots, chambers, dimples, wells or pits.

4. The method according to claim 1, wherein the substrate is of ceramic, glass, quartz or silicon.

5. The method according to claim 1, wherein said device has an area of less than 1 $cm^2$.

6. The method according to claim 1, wherein the area of each reaction site is less than 1 $mm^2$.

7. The method according to claim 1, wherein said surface is rendered hydrophobic by reaction with an organosilane.

8. The method according to claim 7, wherein the organosilane has the formula $(RO)_3Si-(CH_2)_n-X$, wherein each R is a hydrocarbyl group, n is an integer, and X is a functional group.

9. The method according to claim 7, wherein the method includes the use of a bifunctional cross-linker to facilitate covalent attachment of biological ligands to the organosilane.

10. The method according to claim 7, wherein a photolabile cross-linker is used to react with the organosilane having a nucleophilic or electrophilic terminal group.

11. The method according to claim 1, wherein the step of applying the ligands comprises an initial step of derivatizing the hydrophobic surface with macromolecules containing chemical groups that facilitate covalent attachment of the ligands.

12. The method according to claim 11, wherein said macromolecules are selected from the group consisting of polystyrene latex particles, dendrimers and polyethylene glycol.

13. The method according to claim 1, wherein said method additionally comprises applying ligands that bind materials whose presence interferes with assaying an analyte.

14. The method according to claim 1, wherein the substrate is ceramic.

15. The method according to claim 1, further comprising blocking said areas between the reaction sites.

16. The method according to claim 1, wherein said surface is activated and rendered hydrophobic by reaction with an organosilane.

17. The method according to claim 1, said method consisting essentially of:

activating all of said surface of the substrate;

rendering hydrophobic all of said activated surface; and applying an array of ligands onto discrete areas of the hydrophobic surface such that said ligands are not applied to said areas between the reaction sites.

18. The method according to claim 1, said method consisting of:

activating all of said surface of the substrate;

rendering hydrophobic all of said activated surface; and applying an array of ligands onto discrete areas of the hydrophobic surface such that said ligands are not applied to said areas between the reaction sites.

19. A method for forming a solid state device for performing multi-analyte assays comprising a substrate and a multiplicity of discrete reaction sites each bearing a ligand covalently bonded to a surface of the substrate, wherein areas of the surface of the substrate, which are between the reaction sites, are inert with respect to analyte, said method comprising the steps of: rendering hydrophobic all of said surface of the substrate, wherein said surface is an activated surface; and applying an array of ligands onto discrete areas of the hydrophobic surface such that said ligands are not applied to said areas between the reaction sites.

20. The method according to claim 19, wherein said surface is rendered hydrophobic by reaction with an organosilane.

* * * * *